(12) United States Patent
Mitchell et al.

(10) Patent No.: US 6,584,269 B1
(45) Date of Patent: Jun. 24, 2003

(54) FIBER OPTIC CABLE TENSIONING AND POSITIONING APPARATUS

(75) Inventors: David C. Mitchell, Laurel, MD (US); Nolan Scott Cunningham, Frederick, MD (US); Thomas R. Boyer, Gambrills, MD (US)

(73) Assignee: Ciena Corporation, Linthicum, MD (US)

( * ) Notice: Subject to any disclaimer, the term of this patent is extended or adjusted under 35 U.S.C. 154(b) by 0 days.

(21) Appl. No.: 09/844,825

(22) Filed: Nov. 25, 2001

(51) Int. Cl.[7] .............................. G02B 6/44; G02B 6/34; B29D 11/00
(52) U.S. Cl. ........................... 385/136; 242/920; 385/37
(58) Field of Search .............................. 385/136–137, 385/37; 242/147 R, 149, 151, 920

(56) References Cited

U.S. PATENT DOCUMENTS 6,360,042 B1 * 3/2002 Long ........................... 385/37
6,396,994 B1 * 5/2002 Philipson et al. ........... 385/136

* cited by examiner

*Primary Examiner*—Robert H. Kim
*Assistant Examiner*—Krystyna Suchecki

(57) ABSTRACT

A fiber optic cable tensioning and positioning apparatus includes a base, and a vertical support wall integrally connected to the base. A first support connects to a portion of the vertical support wall and supports a first portion of the fiber optic cable. A first clamp attaches to the first support for securing the first portion of the fiber optic cable to the first support. A second support connects to another portion of the vertical support wall and supports a second portion of the fiber optic cable. The second support is pivotally connected to the vertical support wall. A second clamp attaches to the second support for securing the second portion of the fiber optic cable to the second support. A knob also pivotally connects to the vertical support wall, and is connected to a cam. The cam contacts the second support, wherein the second support rotates due to its weight and the weight of the second clamp when the cam is in a predetermined position, thereby uniformly tensioning and positioning the fiber optic cable. The fiber optic cable tensioning apparatus is useful for uniformly and repeatably tensioning a fiber optic cable to precisely position the fiber optic cable prior to creation of a refractive-index grating in the glass optical fiber of a portion of the fiber optic cable.

19 Claims, 4 Drawing Sheets

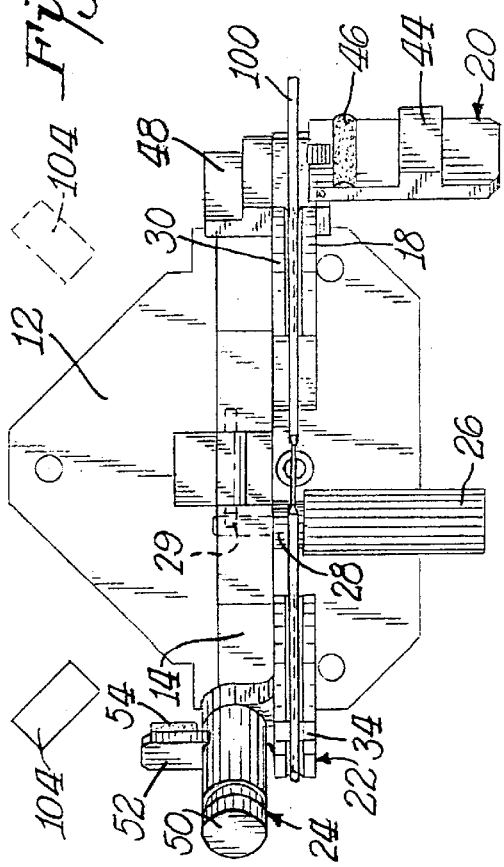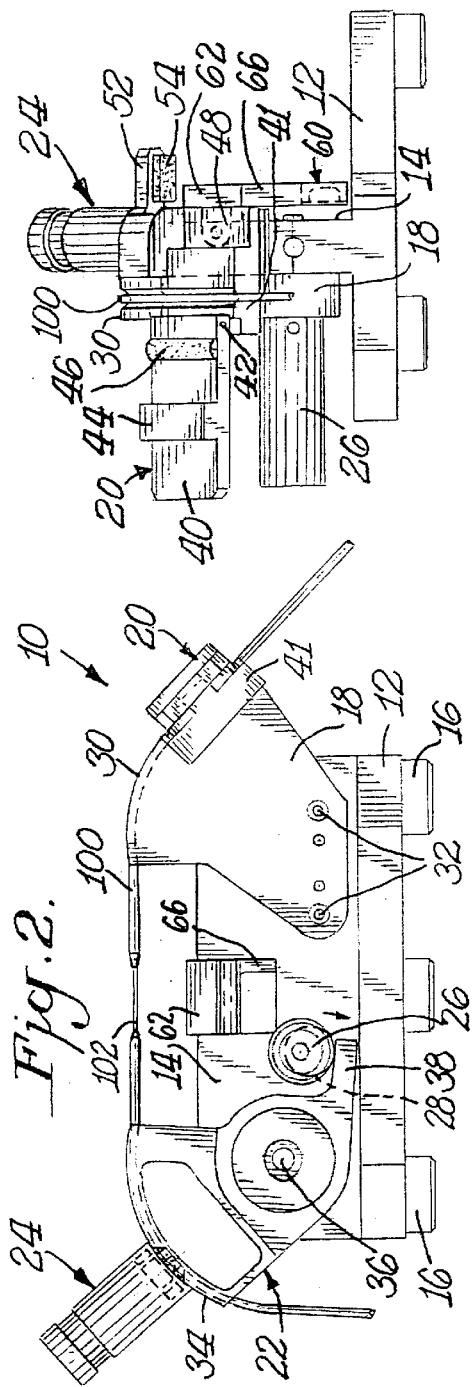

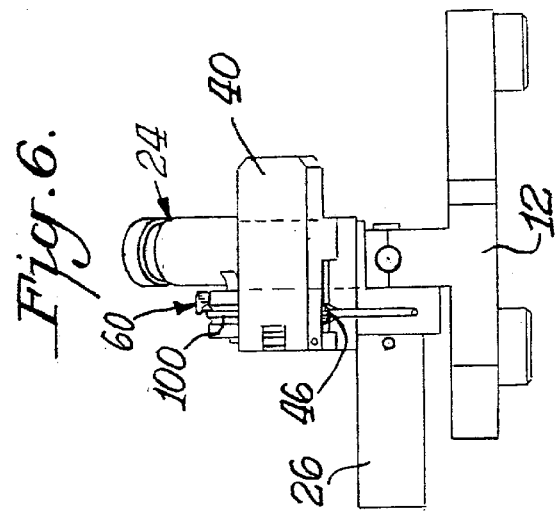
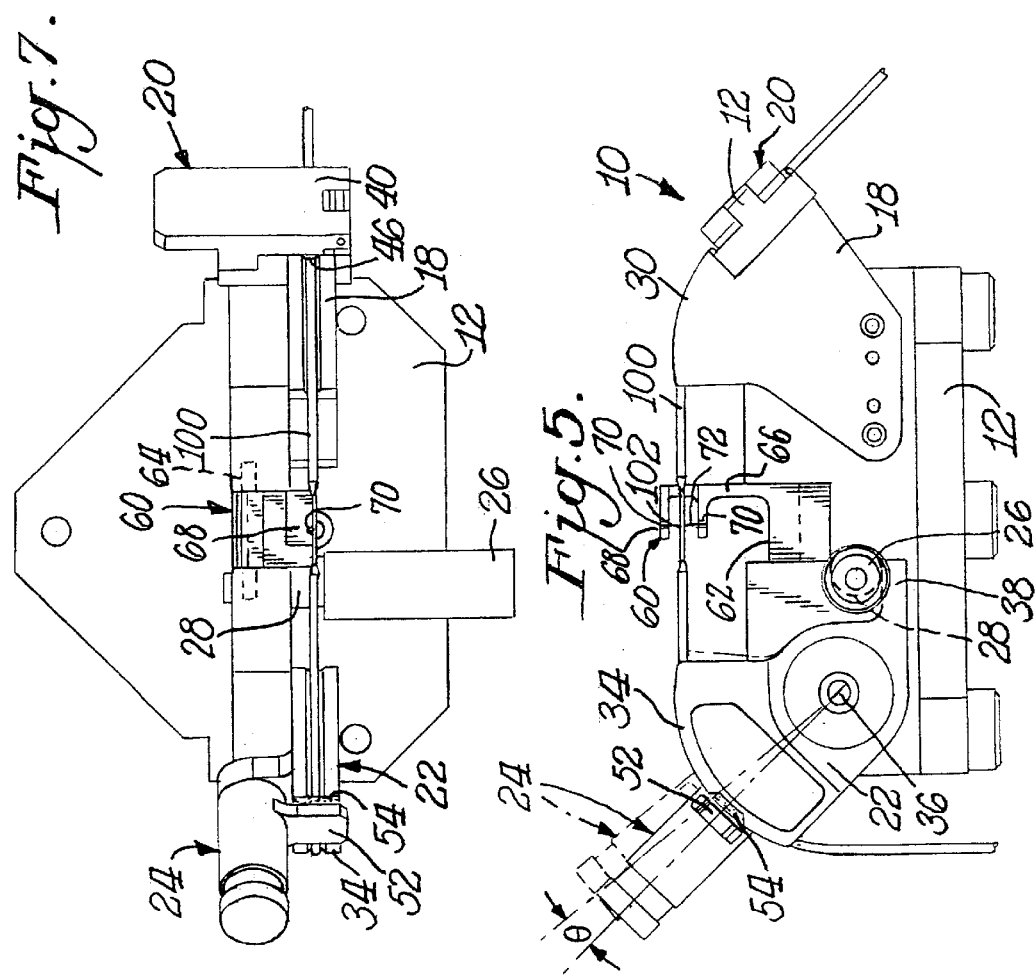

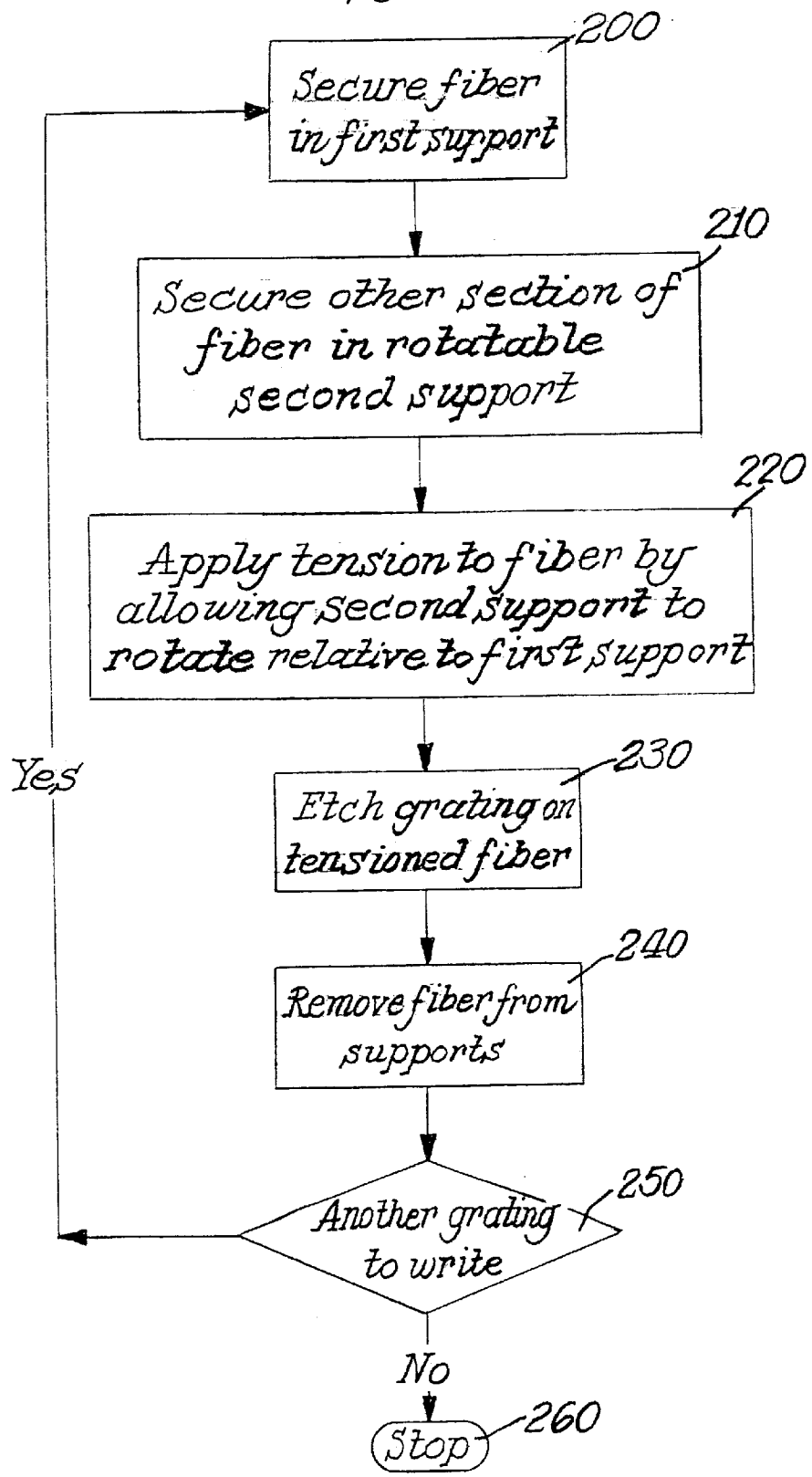

FIBER OPTIC CABLE TENSIONING AND POSITIONING APPARATUS

BACKGROUND OF THE INVENTION

A. Field of the Invention

The present invention relates generally to the communications field, and, more particularly to a fiber optic cable tensioning and positioning apparatus and method for tensioning and positioning a fiber optic cable using the same.

B. Description of the Related Art

Along with the increasing prominence of the Internet has come the wide-ranging demand for increased communications capabilities, including more channels and greater bandwidth per channel. Optical media, such as fiber optic cables, promise an economical alternative to electrical conductors for high-bandwidth long-distance communications. A typical fiber optic cable includes a silica core (glass optical fiber), a silica cladding, and a protective coating. The glass optical fibers of fiber optic cables have very small diameters, which are susceptible to external influences such as mechanical stress and environmental conditions. The index of refraction of the core is higher than the index of refraction of the cladding to promote internal reflection of light propagating down the core.

An optical fiber diffraction grating can output light having a specific reflection wavelength upon reception of incident light. Owing to this advantage, a great deal of attention has recently been paid to the optical fiber diffraction grating as an important optical part in a wavelength division multiplex (WDM) optical transmission communication system which multiplexes and transmits optical signals having different wavelengths through one optical fiber.

The signal carrying ability of fiber optic cables is due in part to the capability of producing long longitudinally-uniform optical fibers. However, longitudinal variations in index of refraction, e.g., those associated with refractive-index gratings, can be included in the fiber optic cables to affect throughgoing pulses in useful ways. Gratings can be grouped into short-period, e.g., about 0.5 micron ($\mu$m), or long-period, e.g., about 200 $\mu$m, gratings. Short-period gratings can reflect incident light of a particular wavelength back on itself in the fiber. Long-period gratings can couple incident light of a particular wavelength into other co-propagating modes on the fiber. Some of these other co-propagating modes may be lost, so the overall effect of the long-period grating can be to selectively block certain wavelengths from propagating efficiently through the fiber.

While there are many methods for establishing a diffraction (or refractive-index) grating within a fiber, one method involves exposing photosensitive glass optical fibers to patterned light, via lasers. The index of refraction of certain fiber-optic materials, such as germanium-doped silica, is changed upon exposure to mid-ultra-violet (mid-UV) light, e.g., wavelengths between 190 nanometers (nm) and 270 nm. The lasers are used to etch lines in the glass optical fiber that is exposed (the coating removed) in the fiber optic cable.

In order to precisely form a refractive-index grating within a fiber, it is preferable to apply a repeatable, uniform tension on the fiber optic cable. A uniform tension ensures that the grating period is consistent across the grating length. A repeatable tension ensures grating period consistency from fiber to fiber. If different tensions are applied from one fiber to the next, the fibers will relax by different amounts and thereby cause different spacings between grating lines. In other words, the fiber is somewhat elastic and will stretch when tension is applied and relax when the tension is released. Thus, applying inconsistent amounts of tension to a series of fibers being etched will result in an inconsistent grating period. The grating period tolerance for optical communications equipment is extremely demanding and will not admit such inconsistencies.

Another preferable feature would be to have an apparatus that is able to precisely position the fiber in a repeatable manner. Otherwise, the grating laser beam(s) will need to be aligned for each etching which slows down the manufacturing process and is quite inefficient.

Tensioning the fiber may also help reduce grating period inconsistencies in another way. More specifically, if the fiber is allowed to sag between two points it will form a catenary curve. Projecting a planar grating pattern on a catenary curve may result in a change in grating period across the grating length. Tensioning the fiber reduces or even eliminates the curvature of the catenary and, thereby, improves the grating period consistency. A repeatable tension force further improves grating period consistency from one fiber etching to the next.

Conventional fiber tensioning apparatuses must be finessed by a technician to tension the fiber optic cable. Thus, these apparatuses suffer from the potential for human error and fail to provide a repeatable, uniform tension in the fiber optic cable while etch lines are formed in the glass optical fiber. Even if a skilled technician accurately tensions a particular fiber optic cable, it is virtually impossible for the technician to provide the same tension for a series of cables.

Thus, there is a need in the art to provide an apparatus and a method for accurately and consistently tensioning a fiber optic cable, as well as uniformly tensioning a series of fiber optic cables that are to have identical refractive-index gratings.

SUMMARY OF THE INVENTION

The present invention solves the problems of the related art by providing an apparatus and method for uniformly and consistently tensioning and positioning a fiber optic cable that eliminates the potential for human error by a technician. The apparatus of the present invention relies upon gravity to provide a uniform, repeatable tension to a fiber optic cable, as will be described more fully below. The apparatus is thus useful for uniformly tensioning a multitude of fiber optic cables that are to have identical refractive-index gratings.

In accordance with the purpose of the invention, as embodied and broadly described herein, the invention comprises a fiber optic cable tensioning apparatus, including: a first support for supporting a first portion of the fiber optic cable; a first clamp attached to the first support for securing the first portion of the fiber optic cable to the first support; a second support for supporting a second portion of the fiber optic cable, the second support being rotatable relative to the first support; a second clamp attached to the second support for securing the second portion of the fiber optic cable to the second support; and a cam contacting the second support, wherein the second support rotates due to its weight and the weight of the second clamp when the cam is in a predetermined position, thereby uniformly tensioning the fiber optic cable.

Further in accordance with the purpose of the invention, as embodied and broadly described herein, the invention comprises a fiber optic cable tensioning apparatus, including: a base; a vertical support wall integrally connected to the base; a first support connected to a portion of the vertical support wall and supporting a first portion of the fiber optic cable; a first clamp attached to the first support for securing the first portion of the fiber optic cable to the first support; a second support connected to another portion of the vertical support wall and supporting a second portion of the fiber optic cable, the second support being rotatable relative to the vertical support wall; a second clamp attached to the second support for securing the second portion of the fiber optic cable to the second support; a knob pivotally connected to the vertical support wall; and a cam connected to the knob and contacting the second support, wherein the second support rotates due to its weight and the weight of the second clamp when the cam is in a predetermined position, thereby uniformly tensioning the fiber optic cable.

Still further in accordance with the purpose of the invention, as embodied and broadly described herein, the invention comprises a system for forming a refractive-index grating in a fiber optic cable, including: a laser for etching grating lines in the fiber optic cable; a fiber optic cable tensioning apparatus, having: a first support for supporting a first portion of the fiber optic cable, a first clamp attached to the first support for securing the first portion of the fiber optic cable to the first support, a second support for supporting a second portion of the fiber optic cable, the second support being rotatable relative to the first support, a second clamp attached to the second support for securing the second portion of the fiber optic cable to the second support, and a cam contacting the second support; wherein the second support rotates due to its weight and the weight of the second clamp when the cam is in a predetermined position, thereby uniformly tensioning the fiber optic cable, and the laser etches grating lines in the fiber optic cable after the fiber optic cable has been uniformly tensioned.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 is a side elevational view of the fiber optic cable tensioning apparatus shown in FIG. 1, with fiber clamps in an open position for receiving a fiber optic cable;

FIG. 3 is a right side elevational view of the apparatus shown in FIG. 2;

FIG. 4 is a top plan view of the apparatus shown in FIGS. 2 and 3;

FIG. 5 is a side elevational view of the fiber optic cable tensioning apparatus shown in FIG. 1, with fiber clamps in a closed position and the fiber optic cable in tension;

FIG. 6 is a right side elevational view of the apparatus shown in FIG. 5;

FIG. 7 is a top plan view of the apparatus shown in FIGS. 6 and 7;

FIG. 9 is flow chart showing a method of tensioning a fiber optic cable in accordance with an embodiment of the present invention.

DETAILED DESCRIPTION OF THE PREFERRED EMBODIMENTS

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 1:
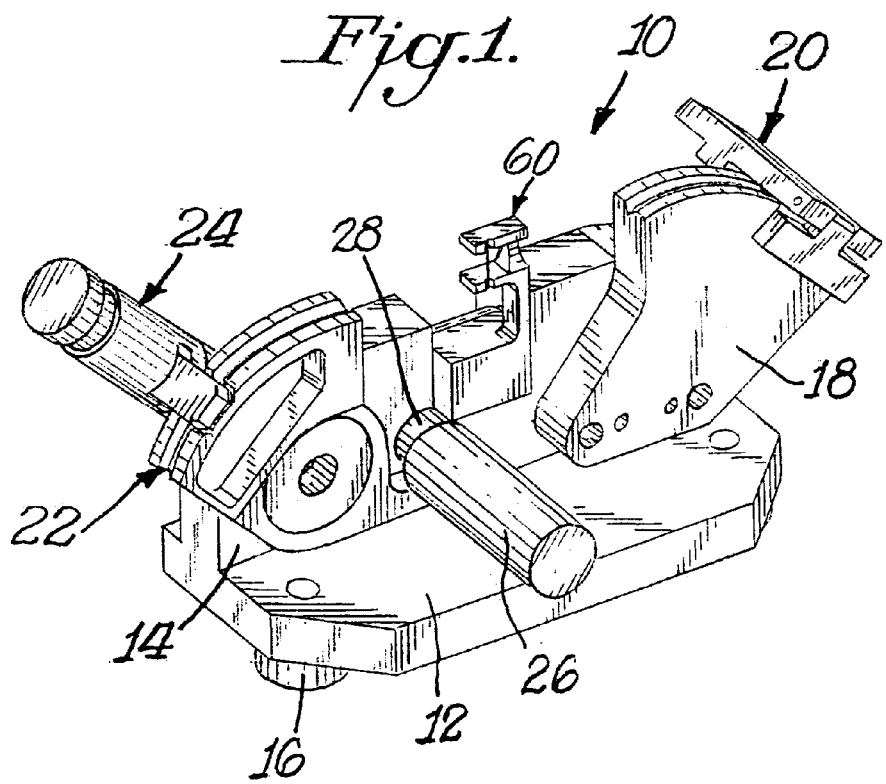
FIG. 1 is perspective view of a fiber optic cable tensioning apparatus in accordance with an embodiment of the present invention.

Referring now specifically to the drawings, a fiber optic cable tensioning and positioning apparatus according to the present invention is illustrated in FIG. 1, and shown generally as reference numeral 10. The tensioning apparatus 10 includes a horizontal base 12 integrally connected to a vertical support wall 14. A plurality of feet 16 supports base 12. A first fiber optic cable support 18 is rigidly affixed to a portion of vertical support wall 14. A first fiber optic cable clamp 20 connects to a portion of first fiber optic cable support 18.

A second fiber optic cable support 22 pivotally attaches to a portion of vertical support wall 14 and is spaced from first fiber optic cable support 18. A second fiber optic cable clamp 24 connects to a portion of second fiber optic cable support 22. Apparatus 10 further includes a knob 26 connected to a cam 28. Both knob 26 and cam 28 pivotally attach to vertical support wall 14, wherein rotation of knob 26 causes cam 28 to rotate. Apparatus 10 also includes an alignment mechanism 60 pivotally attached to vertical support wall 14.

FIGS. 2–4 show the tensioning apparatus 10 as a fiber optic cable 100 is initially provided into apparatus 10, and before fiber optic cable 100 is tensioned. As shown in FIG. 2, first fiber optic cable support 18 includes a grooved curved portion 30 (grooves best shown in FIG. 3) for receiving a first portion of fiber optic cable 100. Preferably, the radius of curvature of grooved curved portion 30 is greater than the minimum bend radius of cable 100. First fiber optic cable support 18 is rigidly attached to vertical support wall 14 via a plurality of conventional attaching means 32 (e.g., screws, rivets, bolts, etc.).

Second fiber optic cable support 22 includes a grooved curved portion 34 (grooves best shown in FIG. 4) for receiving a second portion of fiber optic cable 100. Preferably, the radius of curvature of grooved curved portion 34 is also greater than the minimum bend radius of cable 100. Second fiber optic cable support 22 pivotally attaches to vertical support wall 14 via a pivot pin 36 extending through vertical support wall 14. Preferably, a low-friction bearing (not shown) is provided within pivot pin 36 to ensure pivot pin 36 freely pivots.

Similarly, knob 26 and cam 28 pivotally attach to vertical support wall 14 via a pivot pin 29 provided through vertical support wall 14. Knob 26 is concentrically mounted on pivot pin 29, whereas cam 28 is not centered on pivot pin 29. Second fiber optic cable support 22 further includes a leg portion 38 that is forced downward by cam 28 when cam 28 is in the position shown in FIG. 2. This permits a technician to load fiber optic cable 100, without tensioning cable 100. As further shown in FIG. 2, the exposed glass optical fiber 102 of fiber optic cable 100 is located between first and second supports 20, 22, and ideally centered between supports 20, 22.

As best shown in FIGS. 5–7, alignment mechanism 60 includes a base portion 62 pivotally attached to vertical support wall 14, via pivot pins 64. An arm portion 66 extends away from and is integral with base portion 62. A head portion 68 is integral with and connects to arm portion 66. Head portion 68 has two notches 70 formed therein for receiving and holding a wire 72. Alignment mechanism 60 may be pivoted away from vertical support wall 14 (as shown in FIGS. 2–4), or toward vertical support wall 14 (as shown in FIGS. 5–7). Alternatively, the alignment mechanism 60 may be constructed with no pivotal attachment. In other words, the alignment mechanism 60 may be fixed in place and not allowed to pivot by, for example, eliminating the pivotal attachment and pivot pins 64.

FIG. 3 shows first fiber optic cable clamp 20 in an open position so that fiber optic cable 100 may be received in curved portion 30 of first fiber optic cable support 18. First fiber optic cable clamp 20 includes a body portion 40 pivotally attached to a foot portion 41 by a pivot 42. A protrusion 44 extends away from a surface of and is integral with body portion 40, and may comprise or contain a magnetic material. A stop 46 also extends away body portion 40, and may comprise an elastomeric or resilient material such as rubber. First fiber optic cable clamp 20 further includes a receiving portion 48 that may be made of a metallic material or a magnetic material having a polarity opposite of the polarity of magnetic protrusion 44. When clamp 20 is closed, stop 46 is received in the grooves of curved portion 30 of first fiber optic cable support 18 and fiber optic cable 100 is compressed between stop 46 and curved portion 30, and magnetic protrusion 44 is received in receiving portion 48. The magnetic force created between magnetic protrusion 44 and receiving portion 48 holds clamp 20 closed, and securely compresses cable 100 between stop 46 and curved portion 30.

FIG. 4 shows second fiber optic cable clamp 24 in an open position so that fiber optic cable 100 may be received in curved portion 34 of second fiber optic cable support 22. Second fiber optic cable clamp 24 includes a spring-biased cylindrical portion 50 having an extension 52 integral with and extending away therefrom. A stop 54 is provided on a portion of extension 52 and may comprise an elastomeric or resilient material such as rubber. Clamp 24 may be opened (as shown in FIG. 4) by lifting cylindrical portion 50 upward and rotating extension 52 away from curved portion 34. Cylindrical portion 50 connects to the spring housed therein, and the spring force of the spring forces cylindrical portion 50 toward curved portion. Thus, to open clamp 24 a force must be exerted upon cylindrical portion 50 to overcome the spring force of the spring. When clamp 24 is closed, stop 54 is received in the grooves of curved portion 34 of second fiber optic cable support 22 and fiber optic cable 100 is compressed between stop 54 and curved portion 34. The spring force created by the spring on cylindrical portion 50 holds clamp 22 closed, and securely compresses cable 100 between stop 54 and curved portion 34.

At least one magnetic clamp 20 is preferably used with apparatus 10 since magnetic clamp 20 is easy to maneuver by a technician when holding two portions of fiber optic cable 100. However, two magnetic clamps 20, two spring-biased clamps 24, or two similar types of clamps may be used with apparatus 10. Furthermore, magnetic clamp 20 may be switched with spring-biased clamp 24.

Figure 8:
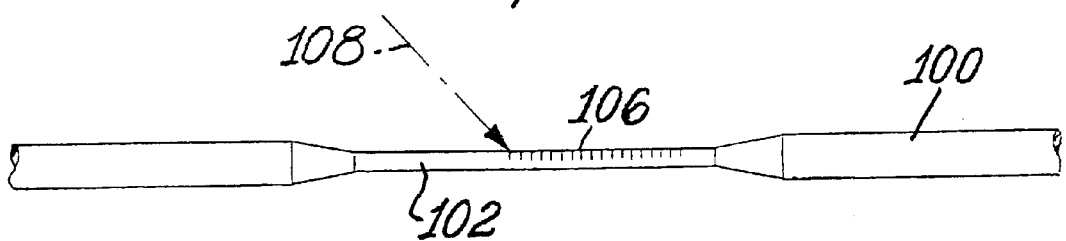
FIG. 8 is an enlarged fragmental side elevational view showing the fiber optic cable etched with refractive-index grating lines.

As further shown in FIG. 4, a pair of laser beams may be provided by a laser 104 located adjacent to the fiber optic cable apparatus 10 to etch lines in the glass optical fiber 102 that is exposed in the fiber optic cable 100 in a conventional etching process, as modified by apparatus 10 of the present invention. Laser 104 is aligned to expose photosensitive glass optical fiber 102 to patterned light emanating therefrom. Laser 104 may be any conventional laser used to form a refractive-index grating within a fiber optic cable. FIG. 8 shows the resulting fiber optic cable 100 and etch lines 106 formed in glass optical fiber 102 by a patterned laser beam 108.

FIGS. 5–7 show the tensioning apparatus 10 as a fiber optic cable 100 is secured in clamps 20, 22 of apparatus 10, and with fiber optic cable 100 in tension. As shown, a first portion of fiber optic cable 100 is secured in first clamp 20, that is, the first portion of cable 100 is compressed between stop 46 of first clamp 20 and curved portion 30 of first support 18. A second portion of fiber optic cable 100 is secured in second clamp 24, that is, the second portion of cable 100 is compressed between stop 54 of second clamp 24 and curved portion 34 of second support 22. Once fiber optic cable 100 is secured in clamps 20, 24, knob 26 is rotated, which in turn rotates cam 28, until cam 28 is located at its position shown in FIG. 5. In this position, cam 28 still contacts leg portion 38 of second support 22, but leg portion 38 has moved upward in comparison to its location shown in FIG. 2. The movement of leg portion 38 causes second support 22 to rotate counterclockwise about pivot pin 36, causing a uniform tension to be applied to fiber optic cable 100.

As shown in FIG. 5, second support 22 rotates counterclockwise at an angle $\theta$. Angle $\theta$ is approximately between five to seven degrees, but may vary depending upon the elastic properties of the fiber optic cable being tensioned and the weights of second support 22 and second clamp 24. A uniform, repeatable tension is applied to cable 100 since second clamp 24 and second support 22 have known weights, and the tension applied to cable 100 is due to gravity acting upon second clamp 24 and second support 22. Second clamp 24 and second support 22 create a moment arm that is opposed by a counter-moment created by cable 100 in a uniform and repeatable manner.

The weights of second clamp 24 and/or second support 22 may be varied to provide different tensions on different fiber optic cable types. This may be accomplished by, for example, constructing the second clamp and/or second support 22 to have a desired weight or by adding removable weight(s) to clamp 24 and/or support 22. Another alternative to varying the amount of tension applied is to increase the length of the moment arm by, for example, constructing the second support 22 and/or second clamp 24 to have a different length or by, for example, constructing second support 22 such that it has a threaded weight at the end that can be screwed into and out of the second support 22 and thereby change the length of the moment arm.

Apparatus 10 may be calibrated using a cable 100 having a known diffraction grating. To calibrate, untensioned cable 100 is provided in apparatus 10, and light having a known wavelength is injected into the untensioned cable 100 with, for example, a laser. The wavelength reflected by the known grating in cable 100 is measured by, for example, an OSA (optical spectrum analyzer). Alternatively, the wavelength measurement of the untensioned cable may be made before loading cable 100 into apparatus 10. Tension is then applied to the cable 100 using the apparatus 10 and another wavelength measurement made. By comparing the wavelength shift (untensioned versus tensioned) and applying conventional equations, the amount of tension applied by the apparatus 10 may be precisely determined. In the same fashion, the repeatability of the tension applied by apparatus 10 to a series of cables 100 may also be assessed.

Although the method of tensioning fiber optic cable 100 has been described above with reference to apparatus 10, a step-by-step description of the method will be described with reference to FIG. 9. With first clamp 20 and second clamp 24 in their open positions and cam 28 in its position shown in FIG. 2, a technician lays the first portion of fiber optic cable 100 in grooved curved portion 30 of first support 18, and then closes first clamp 20, making sure that glass optical fiber 102 is centered on apparatus 10. This secures a portion of cable 100 in first support 18 (step 200). The second portion of cable 100 is then placed in grooved curved portion 34 of second support 22, cable 100 is pulled to eliminate slack, and second clamp 24 is rotated and closed. This secures another portion of cable 100 in second support 22 (step 210). The technician then rotates knob 26 (and thus, cam 28) 180 degrees from its position shown in FIG. 2, or until cam 28 reaches the position shown in FIG. 5. This permits second support 22 to rotate at angle θ, uniformly tensioning fiber optic cable 100 (step 220). The technician may then energize laser 104 and begin the process for etching a refractive-index grating in glass optical fiber 102 of cable 100 (step 230). Once the grating is etched, cable 100 may be removed from apparatus 10 (step 240) by reversing the previous method steps. If another grating is to be written, the method is repeated at step 250, if not, the method is terminated at step 260.

It will be apparent to those skilled in the art that various modifications and variations can be made in the fiber optic cable tensioning apparatus and method of the present invention and in construction of the apparatus and method without departing from the scope or spirit of the invention. As an example, although stainless steel is the preferred material for the components of the apparatus of the present invention, other similarly stable materials may be used. Furthermore, as described previously, the tension applied to cable 100 may be varied to create different diffraction gratings with the present invention. Alternatively, the tension may be held uniform with the present invention, and the wavelength of the laser beams etching the diffraction grating may be varied to create different diffraction gratings.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A fiber optic cable tensioning apparatus, comprising:
a first support for supporting a first portion of the fiber optic cable;
a first clamp attached to said first support for securing the first portion of the fiber optic cable to said first support;
a second support for supporting a second portion of the fiber optic cable, said second support being rotatable relative said first support;
a second clamp attached to said second support for securing the second portion of the fiber optic cable to said second support; and
a cam contacting said second support, wherein said second support rotates due to its weight and the weight of said second clamp when said cam is in a predetermined position, thereby uniformly tensioning the fiber optic cable.

2. A fiber optic cable tensioning apparatus as recited in claim 1, wherein said first support has a grooved portion for receiving the first portion of the fiber optic cable, and said second support has a grooved portion for receiving the second portion of the fiber optic cable.

3. A fiber optic cable tensioning apparatus as recited in claim 1, wherein said first clamp comprises a body portion pivotally attached to a foot portion, the body portion having a stop extending therefrom for securing the first portion of the fiber optic cable against said first support, the body portion further having a magnetic extension that forces body portion against said first support.

4. A fiber optic cable tensioning apparatus as recited in claim 1, wherein said second clamp comprises a spring-biased cylindrical portion having an extension extending therefrom, the extension having a stop extending therefrom for securing the second portion of the fiber optic cable against said second support, and the cylindrical portion being rotatable to permit the fiber optic cable to be loaded onto said second support.

5. A fiber optic cable tensioning apparatus as recited in claim 1, wherein said second support comprises a rotatable body portion integrally connected to a leg portion, the leg portion contacting said cam to rotate said second support.

6. A fiber optic cable tensioning apparatus as recited in claim 1, further comprising an alignment mechanism provided between said first and second supports to align a glass optical fiber portion of the fiber optic cable.

7. A fiber optic cable tensioning apparatus, comprising:
a base;
a vertical support wall integrally connected to said base;
a first support connected to a portion of said vertical support wall and supporting a first portion of the fiber optic cable;
a first clamp attached to said first support for securing the first portion of the fiber optic cable to said first support;
a second support connected to another portion of said vertical support wall and supporting a second portion of the fiber optic cable, said second support being rotatable relative to said vertical support wall;
a second clamp attached to said second support for securing the second portion of the fiber optic cable to said second support;
a knob pivotally connected to said vertical support wall; and
a cam connected to said knob and contacting said second support, wherein said second support rotates due to its weight and the weight of said second clamp when said cam is in a predetermined position, thereby uniformly tensioning the fiber optic cable.

8. A fiber optic cable tensioning apparatus as recited in claim 7, wherein said first support has a grooved portion for receiving the first portion of the fiber optic cable, and said second support has a grooved portion for receiving the second portion of the fiber optic cable.

9. A fiber optic cable tensioning apparatus as recited in claim 7, wherein said first clamp comprises a body portion pivotally attached to a foot portion, the body portion having a stop extending therefrom for securing the first portion of the fiber optic cable against said first support, the body portion further having a magnetic extension that forces body portion against said first support.

10. A fiber optic cable tensioning apparatus as recited in claim 7, wherein said second clamp comprises a spring-biased cylindrical portion having an extension extending therefrom, the extension having a stop extending therefrom for securing the second portion of the fiber optic cable against said second support, and the cylindrical portion being rotatable to permit the fiber optic cable to be loaded onto said second support.

11. A fiber optic cable tensioning apparatus as recited in claim 7, wherein said second support comprises a rotatable body portion integrally connected to a leg portion, the leg portion contacting said cam to rotate said second support.

12. A fiber optic cable tensioning apparatus as recited in claim 7, further comprising an alignment mechanism provided between said first and second supports and connected to said vertical support wall, said alignment mechanism aligning a glass optical fiber portion of the fiber optic cable.

13. A system for forming a refractive-index grating in a fiber optic cable, comprising:
 a laser for etching grating lines in the fiber optic cable;
 a fiber optic cable tensioning apparatus, having:
  a first support for supporting a first portion of the fiber optic cable,
  a first clamp attached to the first support for securing the first portion of the fiber optic cable to the first support,
  a second support for supporting a second portion of the fiber optic cable, the second support being rotatable relative to the first support,
  a second clamp attached to the second support for securing the second portion of the fiber optic cable to the second support, and
  a cam contacting the second support;
 wherein the second support rotates due to its weight and the weight of the second clamp when the cam is in a predetermined position, thereby uniformly tensioning the fiber optic cable, and said laser etches grating lines in the fiber optic cable after the fiber optic cable has been uniformly tensioned.

14. A system for forming a refractive-index grating in a fiber optic cable as recited in claim 13, wherein the fiber optic cable is precisely positioned for etching grating lines when uniformly tensioned.

15. A system for forming a refractive-index grating in a fiber optic cable as recited in claim 13, wherein the first support has a grooved portion for receiving the first portion of the fiber optic cable, and the second support has a grooved portion for receiving the second portion of the fiber optic cable.

16. A system for forming a refractive-index grating in a fiber optic cable as recited in claim 13, wherein the first clamp comprises a body portion pivotally attached to a foot portion, the body portion having a stop extending therefrom for securing the first portion of the fiber optic cable against the first support, the body portion further having a magnetic extension that forces body portion against the first support.

17. A system for forming a refractive-index grating in a fiber optic cable as recited in claim 13, wherein the second clamp comprises a spring-biased cylindrical portion having an extension extending therefrom, the extension having a stop extending therefrom for securing the second portion of the fiber optic cable against the second support, and the cylindrical portion being rotatable to permit the fiber optic cable to be loaded onto the second support.

18. A system for forming a refractive-index grating in a fiber optic cable as recited in claim 13, wherein the second support comprises a rotatable body portion integrally connected to a leg portion, the leg portion contacting the cam to rotate the second support.

19. A system for forming a refractive-index grating in a fiber optic cable as recited in claim 13, wherein said fiber optic cable tensioning apparatus further includes an alignment mechanism provided between the first and second supports to align a glass optical fiber portion of the fiber optic cable.

* * * * *